(12) United States Patent
Zhao et al.

(10) Patent No.: US 8,673,981 B2
(45) Date of Patent: *Mar. 18, 2014

(54) PHENYLCYCLOBUTYLAMIDE DERIVATIVES AND THEIR STEREOISOMERS, THE PREPARATION PROCESSES AND USES THEREOF

(71) Applicants: Shuqiang Zhao, Haidian District (CN); Shouming Wen, Haidian District (CN); Hao Ding, Haidian District (CN); Yashi Yan, Haidian District (CN); Xiaoping Chen, Haidian District (CN)

(72) Inventors: Shuqiang Zhao, Haidian District (CN); Shouming Wen, Haidian District (CN); Hao Ding, Haidian District (CN); Yashi Yan, Haidian District (CN); Xiaoping Chen, Haidian District (CN)

(73) Assignee: YinGu Pharmaceutical Co., Ltd, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/926,653

(22) Filed: Jun. 25, 2013

(65) Prior Publication Data

US 2013/0289124 A1    Oct. 31, 2013

Related U.S. Application Data

(63) Continuation of application No. 12/810,565, filed as application No. PCT/CN2009/000310 on Mar. 24, 2009, now Pat. No. 8,497,305.

(30) Foreign Application Priority Data

Apr. 8, 2008   (CN) .......................... 2008 1 0103525

(51) Int. Cl.
*A61K 31/165*   (2006.01)
*A61P 3/04*   (2006.01)

(52) U.S. Cl.
USPC ......................................... 514/626; 564/194

(58) Field of Classification Search
USPC ......................................... 514/626; 564/194
See application file for complete search history.

(56) References Cited

U.S. PATENT DOCUMENTS

| 6,127,424 | A | 10/2000 | Martin et al. |
| 2008/0268038 | A1 | 10/2008 | Wolfe |

FOREIGN PATENT DOCUMENTS

WO    2007/073133 A1    6/2007

OTHER PUBLICATIONS

Link, et al. "Metabolite profile of sibutramine in human urine: a liquid chromatography-electrospray ionization mass spectrometric study." Journal of Mass Spectrometry. 41: 1171-1178. Published Aug. 3, 2006.

Lu, et al. "Control of Diastereoselectivity by Solvent Effects in the Addition of Grignard Reagents to Enantiopure t -Butylsulfinimine: Syntheses 'of the Stereoisomers of the Hydroxyl Derivatives of Sibutramine." Organic Letters. vol. 7, No. 13. 2599-2602. Apr. 1, 2005.
Japanese Office Action mailed Jan. 9, 2013 for Japanese Patent Application 2011-516506, 2 pages.
CN OA mailed Jun. 8, 2011 for Chinese Patent Application No. 200810103525.2, 4 pages.
CN OA mailed Nov. 16, 2011 for Chinese Patent Application No. 200810103525.2, 4 pages.
CN OA mailed Feb. 13, 2012 for Chinese Patent Application No. 200810103525.2, 3 pages.
Indian OA dated May 18, 2012 for Indian Patent Application No. 1328/MUMNP/2010, 2 pages.
Notice of Allowance mailed May 12, 2011 for Australian Patent Application No. 2009235887, 3 pages.
Canadian OA mailed Jan. 26, 2012 for Canadian Patent Application No. 2,710,464, 3 pages.
Notice of Allowance mailed Jul. 19, 2012 for Canadian Patent Application No. 2,710,464, 3 pages.
Notice of Allowance mailed May 8, 2012 for Chinese Patent Application No. 200810103525.2, 1 page.
RU OA mailed Dec. 28, 2010 for Russian Patent Application No. 2010139017, 6 pages.
International Search Report for PCT/CN09/000310 mailed on Jul. 9, 2009.

*Primary Examiner* — Renee Claytor
*Assistant Examiner* — Sahar Javanmard
(74) *Attorney, Agent, or Firm* — Turocy & Watson, LLP

(57) ABSTRACT

Phenylcyclobutylamide derivatives and their optical isomers, the preparing processes and the uses thereof, which includes the compounds of formula (I), their pure stereoisomers and their pharmaceutically acceptable salts. In formula (I), R is H, formacyl, acetyl, haloacetyl, benzoyl, benzyloxy carbonyl (Cbz), t-butoxy carbonyl (Boc), or 9-fluorenyl methoxy carbonyl (Fmoc). The present novel compounds have pharmaceutical activity and are prepared by condensation reaction of racemic, levo- or dextro-demethyl Sibutramine and racemic or D/L isoleucine under a mild condition. It is demonstrated that the present compounds have effect of losing weight to obese mode rats in different level and the effect is better than Sibutramine by the animal experiments. So the medicaments prepared by the present compounds or the medicaments prepared by the compositions of the present compounds and other pharmaceutical activity compounds may be used for treating obesity.

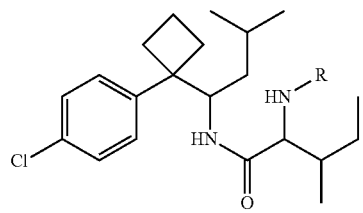

6 Claims, No Drawings

US 8,673,981 B2

PHENYLCYCLOBUTYLAMIDE DERIVATIVES AND THEIR STEREOISOMERS, THE PREPARATION PROCESSES AND USES THEREOF

CROSS-REFERENCE TO RELATED APPLICATIONS

This application is a Continuation of application Ser. No. 12/810,565 filed on Jun. 25, 2010, which is a 35 U.S.C. §371 National Phase application of PCT International application No. PCT/CN2009/000310 filed on Mar. 24, 2009, the entire contents of both of which are incorporated herein by reference.

This application is based upon and claims the benefit of priority from the prior Chinese Patent Application No. 200810103525.2 filed on Apr. 8, 2008, the entire contents of which are incorporated herein by reference.

FIELD OF THE INVENTION

The present invention belongs to the field of chemical medicine and specifically relates to new stereoisomers of phenylcyclobutylamide derivatives and their pharmaceutically acceptable salts. The present invention also relates to preparation methods of the stereoisomers and salts thereof, pharmaceutical compositions comprising the stereoisomers and salts thereof, and the use of these stereoisomers, salts and compositions in preparation of medicines for treating obesity.

BACKGROUND OF THE INVENTION

With the improvement of people's living standards, obesity resulting from unreasonable diet becomes more and more acutely in daily life. Experts from the Obesity Society are recognizing obesity as a global obesity epidemic, and its rate is rising increasingly. According to a document of the WHO, 1 billion people are overweight and at least 300 million people are obese. Obesity happens not only in the developed countries, but also in the developing countries. In the 11th European congress on obesity, China has been included into the Ranking of Obesity Rate for the first time. Obesity, as well as AIDS, drug and alcohol addiction are considered four dangerous social problems for human health in the world. It may provocate or aggravate the incidence of some common chronic diseases, especially diabetes, cardiovascular system diseases, and sleep apnea syndrome. Statistics show that in the past 10-20 years 280,000-325,000 people die per year because of obesity or its complications. Although the development of a sense of self-care people can use many ways to control weight, such as regular exercise in accompany with reasonable diet, few have long-term beneficial effects. Therefore a weight-reducing drug is increasingly desired, and thus developing safe and effective weight-loss drugs will bring extraordinary social and economic returns.

Sibutramine hydrochloride, 1-(4-chlorophenyl)-N,N-dimethyl-α-(2-methylpropyl)cyclobutanemethanamine hydrochloride monohydrate, is a weight-loss drug developed by Konll Company (BASF, Germany), and is a serotonin-noradrenalin reuptake inhibitor. In November 1997, Sibutramine hydrochloride was given approval as weight-loss drug by F.D.A. and then went on market in February 1998 with brand name of Meridia. In the same year 1998, sales amount of Meridia was 194 million US dollars, and rose to more than 300 million US dollars in 1999. Meridia has been one of the mainstream products over European and US weight-loss market and sold well in nearly 20 countries. Meridia has been one of the four main products of BASF. In May 2000, this product received the approval by SDA in China with brand name of QuMei. Until now, there are nearly 3 million people taking Sibutramine hydrochloride over the world.

Sibutramine HCl is a serotonin-noradrenalin reuptake inhibitor (Buckett, W. R., Thomas, P. C., Luscombe, G. P., Prog. Neuropsychopharmacol. Biol. Psychiat, 1988, 12: 575-584; Luscombe, G. P., Hoperoft, R. H., Thomas, P. C., Buckett, W. R., Neuropharmacology, 1989, 28: 129-134). It is confirmed that Sibutramine Hydrochloride can reduce weight by a two-way effect. On one hand, it can increase satiety to decrease food consumption (Fantino, M., Souquet, A.-M., Int. J. Obesity, 1995, 19: 145; Halford, J. C. G, Heal, D. J., Blundell, J. E., Brit. J. Pharmacol 1995, 114: 387P; Stricker-Krongrad, A., Souquet, A.-M., Burlet, C., Int. J. Obesity, 1995, 19: 145). On the other hand, it can stimulate heat production to enhance energy consumption (Connoley, I. P., Heal, D. J., Stocl, M. J., Brit. J. Pharmacol, 1995, 114: 388P; Connoley, I. P., Frost, I., Heal, D. J., Stocl, M. J., Brit. J. Pharmacol, 1996, 117: 170P). Additionally, Sibutramine hydrochloride can decrease waist-hip ratio, and at the same time reduce the concentration of triglyceride, total cholesterol, and LDL-ch in blood, and increase the concentration of HDL-ch in blood (Qifu Lee, et al., Chinese Journal of Endocrinology and Metabolism, 2002, 18(3): 204-205; Jian Wu, et al., Medical Journal of Chinese People's Liberation Army, 2002, 27(2):172-176; Jian Wu, et al., Chinese Journal of Endocrinology and Metabolism, 2001, 18(3): 201-202).

It has been revealed that Sibutramine HCl can reduce 5%-10% basal weight and retain weight loss very well. Sibutramine hydrochloride did not show obviously sedative, stimulant or adrenergic effects, and had good drug tolerance. However, dry mouth, headache, anorexia, constipation and insomnia would be the side effects.

It has been further revealed that Sibutramine HCl and its demethylated derivative can treat nervous and mental diseases such as obesity, insomnia, tiredness, depression and the like; metabolic diseases; and cardiovascular diseases. For Sibutramine HCl, its stereoisomers and its demethylated derivative, PCT/US2000/007202 has disclosed that they can decrease the weight gain after pregnancy; PCT/US2000/007255 has disclosed that they can reduce platelet adhesion; PCT/US2000/007122 has disclosed their treatment on chronic fatigue syndrome; PCT/US2000/007123 has disclosed their treatment on metabolic syndrome; PCT/US2000/007361 has disclosed their effect on obesity related tumor; PCT/US2000/007124 has disclosed their treatment on pulmonary hypertension; PCT/US2000/007177 has disclosed their treatment on sleep syndrome; PCT/US2000/001217 has disclosed their action on smoking cessation; U.S. Pat. No. 6,046,242 has disclosed their treatment on urinary incontinence. It has been provided many methods to resolve the enantiomers of Sibutramine HCl in large scale (Tetra Asymm 2003, 14(25): 3553-3556).

In addition, researchers in the chemical synthesis field have also provided many methods of modifying Sibutramine HCl, such as routes of asymmetric synthesis of R-sibutramine (Organic process research and development 2006, 10(2): 327-333); demethylation methods of sibutramine (U.S. Pat. No. 6,399,826); asymmetric synthesis of demethylated R-sibutramine (Tetra Lett, 2002, 43(13): 2331-2333). Researches on individual modification of methyl, amino and cyclobutyl of demethylated sibutramine and preparation of pure optical isomer of above derivatives were also provided (J. Chem. Soc. Perkin Trans. 1; EN; 21; 1996; 2583-2590). In the literature, Org. Lett. 2005: 2599-2602, methyl and amino of demethylated sibutramine were modified, and optical isomer of this derivative was resolved.

However, above researches only relate to the chemical moiety of the sibutramine modified derivatives. There is no literature that relates to the acidification of the amino of double-demethylated sibutramine derivatives. Further, there is no literature focusing on deep research on weight loss effect of sibutramine derivatives or comparison between their enantiomers.

SUMMARY OF THE INVENTION

An aspect of the present invention is to provide new phenylcyclobutylamide derivatives. New compounds as well as their optical isomers are obtained through the amino acid acylation of free amino of double-demethylated sibutramine, with the weight loss effect of the new compounds being evaluated by pharmacodynamics.

Phenylcyclobutylamide derivatives of the present invention include compounds of Formula (I), pure stereoisomers and pharmaceutically acceptable salts thereof.

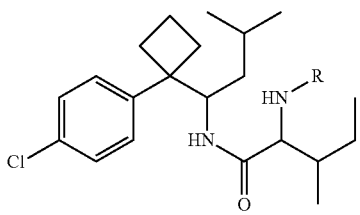

(I)

As shown in Formula (I), the molecule has three asymmetric centers. Besides the racemic mixtures, amino acid side chain of the compound of the present invention is (D)- or (L)-isoleucine derivative. Therefore, four new stereoisomers are included in this invention:

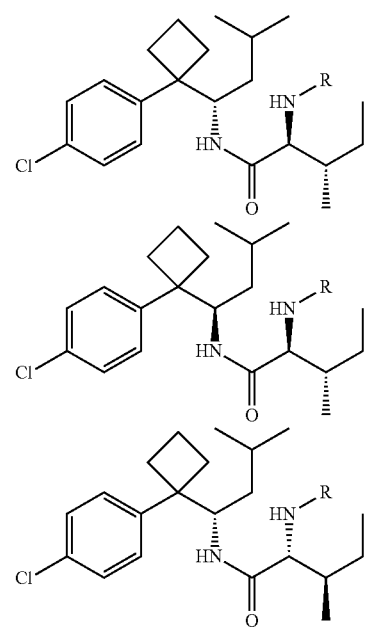

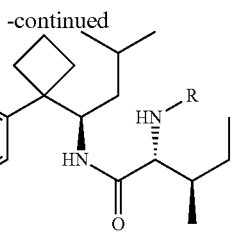

wherein R is H, formacyl, acetyl, haloacetyl, benzoyl, benzyloxycarbonyl (Cbz), t-butyloxycarbonyl (Boc) and 9-fluorenylmethoxycarbonyl (Fmoc).

The present invention also includes a pharmaceutical composition of above phenylcyclobutylamide derivatives, a pharmaceutical composition comprising above phenylcyclobutylamide derivatives as active component in combination with other pharmaceutical accessories, a health care product comprising above phenylcyclobutylamide derivatives as active component in combination with other ingredients, a functional food or drink comprising above phenylcyclobutylamide derivatives as functional components in combination with other ingredients, and a compounding medicine, a compounding health care product, a functional food or drink combining above phenylcyclobutylamide derivatives and other pharmaceutical active compounds.

In addition, an obese rat model is used in the present invention to investigate the weight loss effect of the test compounds and the differences in blood fat, blood biochemistry and organ pathology tests such as heart, liver, kidney and the like compared with the sibutramine HCl control groups. And it is showed that all test compounds have weight loss effect on the obese rats to a distinct extent, and that significant impact on total serum protein and blood sugar of experiment animals are not found, and that no obvious pathological damages to critical organs are also found. Therefore, compounds of this invention are suitable to prevent and cure obesity and related diseases.

Furthermore, this invention provides compounds of Formula (I), their pure stereoisomers, their pharmaceutically acceptable salts, as well as effects on obesity and related diseases of pharmaceutical compositions comprising above compounds and other pharmaceutical active compounds. Related diseases refer to the disorders related to obesity, which are known by the technologist in this field. This term includes but not limited to: hypertension, coronary artery thrombosis, apoplexy, melancholis, anxietas, psychosis (e.g. schizophrenia), tardive dyskinesia, drug addiction, drug abuse, cognitive impairment, alzheimer's disease, cerebrum ischemia, aphrenia, parkinson's disease, forgetful syndrome, compulsion, panic, social phobia, diet disorders, lipid syndrome, exorbitance blood sugar, exorbitance blood fat, and mammal especially human stress response.

In the present invention, demethylated D- or L-sibutramine are condensed with D/L-isoleucine under mild conditions to give a new pharmaceutical active compound. Said compound is a new amide whose structure is different from alkylamino substituted structure of sibutramine HCl. Through the animal model experiment, it is suggested that all of the compounds of this invention have weight loss effect in distinct extents on the rat obesity model, and the effect is even better than sibutramine HCl. Therefore, the medicine prepared from the compounds of the present invention or the pharmaceutically acceptable salts thereof, or the medicine prepared from the composition comprising the compounds of the present invention and other pharmaceutical active compounds, can be used in treatment of obesity.

DETAILED DESCRIPTION OF THE PREFERRED EMBODIMENTS

The following general methodology may be employed to prepare the compounds of this invention.

Method A: Preparation of Racemic Phenylcyclobutylamide Derivatives

Racemic 1-[1-(4-chlorophenyl)cyclobutyl]-3-methylbutylamine (compound II) synthesized according to the method described in Chinese Journal of Pharmaceuticals, 2001, 32(8): 337-339, was condensed with R-isoleucine under mild conditions to give amino modified phenylcyclobutylamide derivatives (Formula I).

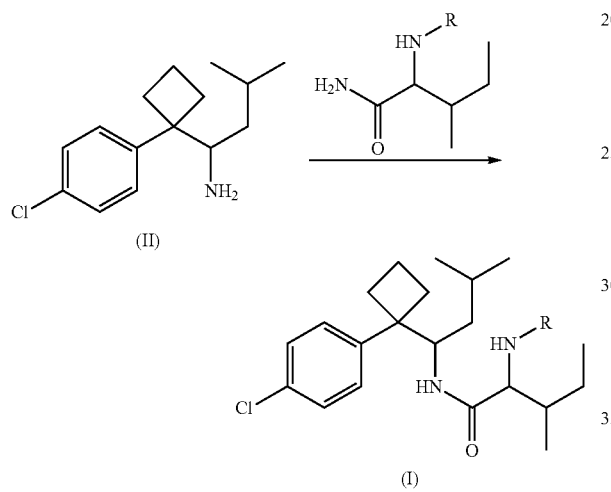

wherein R is formacyl, acetyl, haloacetyl, benzoyl, benzyloxycarbonyl (Cbz), t-butyloxycarbonyl (Boc) or 9-fluorenylmethoxycarbonyl (Fmoc).

Compounds of Formula (I) are independently knocked off formacyl, acetyl, haloacetyl, benzoyl, Cbz, Boc and Fmoc under acidic, basic, or catalytic hydrogenation conditions to give the product which still has the main structure of Formula (I) but wherein R is H. The specific structure is as follows:

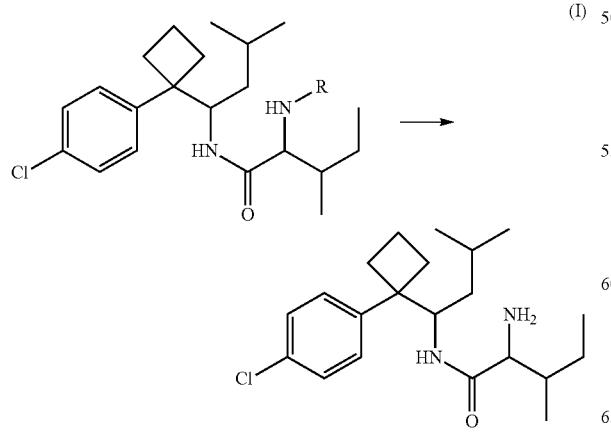

Method B: Preparation of Optical Isomers of Phenylcyclobutylamide Derivatives

Compounds of Formula (I) prepared above are racemic mixtures which can be resolved using known chemical, biological or physical methods to give their corresponding optical isomers (Ye L. X., Stereochemisty, Perking university Press, 1999).

Preparation of Optical Isomers of Phenylcyclobutylamide Derivatives Beginning from Chiral Materials 1-[1-(4-chlorophenyl)cyclobutyl]-3-methylbutylamine (II) has a asymmetric center which can be resolved using tartaric acid or malic acid as chiral agent to give the optical isomers of 1-[1-(4-chlorophenyl)cyclobutyl]-3-methylbutylamine (II-R or II-S), for example, by forming separatable diastereotopic salts or complex crystal, or by forming diastereotopic derivatives which can be separated by crystallization, gas/liquid chromatography or liquid chromatography.

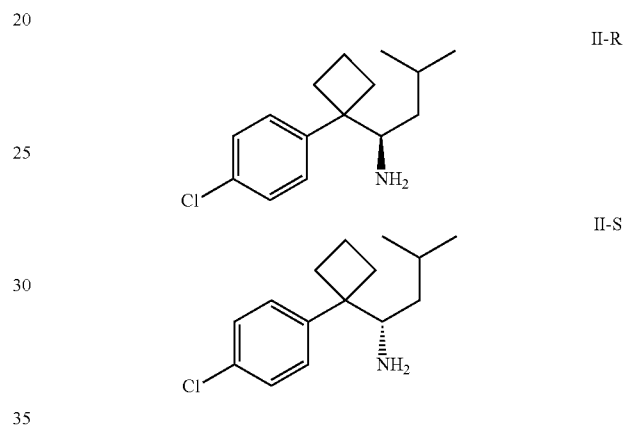

One enantiomer is selectively reacted with chiral agent through methods such as enzymatic oxidation or reduction, and then modified enantiomer is separated from non-modified enantiomer; or the reaction is processed under chiral conditions such as using chiral carrier (e.g. silica gel bound chiral ligand) or using gas-liquid chromatography or liquid chromatography separation method in chiral solvent. It can be understood easily that whatever separation method is used herein, additional step to release corresponding enantiomer is needed.

1-[1-(4-chlorophenyl)cyclobutyl]-3-methylbutylamine (II-R or II-S) is condensed with L/D-isoleucine under mild conditions to give single enantiomer of Formula (I). Wherein R is formacyl, acetyl, haloacetyl, benzoyl, Cbz, Boc and Fmoc Compounds of Formula (I) are independently knocked off formacyl, acetyl, haloacetyl, benzoyl, Cbz, Boc and Fmoc under acidic, basic, or catalytic hydrogenation conditions to give the product which still has the main structure of Formula (I) but wherein R is H. The specific structures of the optical isomers are as follows:

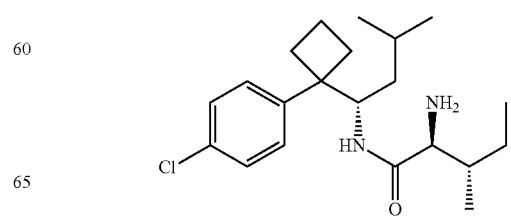

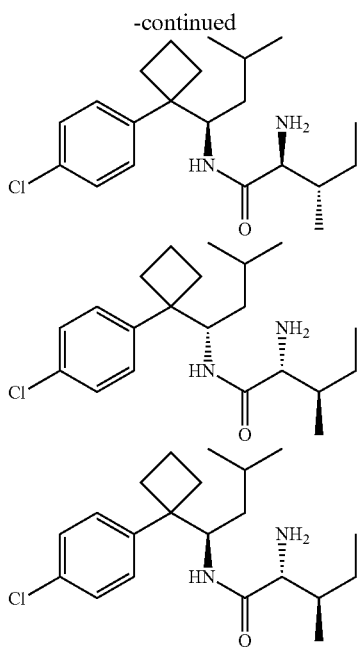

In the preparation of racemic mixtures and enantiomers of the phenylcyclobutylamide derivatives above, a condensation reaction step is related. It will be appreciated by those skilled in the art that many known condensing agents for forming the compounds of the invention are available, such as DCC, DIC, BDP, BOP, EDC, AOP, PyAOP, PPAA, TOTU, HATU, HAPyU, HAMDU, HBTU, HBTyU, HBMDU, HBPyU, DEPBT, HOAT, HOBT, PyBOP, TATU, TBTU, PyBrop, PyCloP, CIP, TFFH, BTFFH, PyCIU, CDTP, BOP-Cl, DPPA, DEPC, BOMI, BDMP, and the like.

Compounds within the scope of this invention also include pharmaceutically acceptable salts of compounds of Formula (I) and their enantiomers. As compared with the starting or base compounds, the salts thereof have better solubility in water, and thus are suitable in medical applications. The compounds of the present invention contain basic nitrogen, thus the salts thereof can be obtained by reacting with inorganic acids such as hydrochloric acid, hydrobromic acid, hydroiodic acid, phosphoric acid, metaphosphoric acid, nitric acid, sulfonic acid, and sulfuric acid and the like, or with organic acids such as carbonic acid, acetic acid, oxalic acid, benzenesulfonic acid, p-toluene sulfonic acid, p-bromo benzenesulfonic acid, amber acid, benzoic acid, citric acid, ethanesulfonic acid, fumaric acid, gluconic acid, glycolic acid, isethionic acid, lactic acid, lactose acid, maleic acid, malic acid, methanesulfonic acid, succinic acid, p-toluene-sulfonic acid, tartaric acid and trifluoroacetic acid, amino acids and the like, preferably hydrochloric acid. Therefore, these pharmaceutically acceptable salts include sulfate, pyrosulfate, bisulfate salt, sulfite, hydrosulfite, phosphate, biphosphate, dihydric phosphate, metaphosphate, pyrophosphate, chloride, bromide, iodide, acetate, propionate, caprylate, acrylate, formate, isobutyrate, heptylate, caprate, propiolate, oxalate, malonate, succinate, suberate, sebacate, fumarate, maleate, 2-butyne-1,4-dioic acid salt, 3-cyclohexyne-2,5-dioic acid, benzoate, chlorbenzoate, phenylacetate, phenpropionate, phenylbutyrate, citrate, lactate, hippurate, β-hydroxy butyrate, glycolate, maleate, tartrate, methanesulfonate, propanesulfonate, naphthalene-1-sulfonate, naphthalene-2-sulfonate, mandelate, glutamate, arginine, lysine and so on. With regard to the medical aim, the chlorine salts are preferably used.

The compounds of the present invention also comprise various polymorphs, such as amorphous form and crystalline form. All forms of the compounds of the present invention are included in the scope of the present invention, which constitutes another aspect of the present invention.

Another aspect of this invention is the uses of compounds of present invention, which include racemic mixtures, optical isomers and pharmaceutically acceptable salts thereof, in the preparation of medicine. In practice, in order to obtain desired biological effects, the required amount depends on various factors, such as the specific compound selected, the expected application, the type of the administration, and the clinical situation of the patient. Generally, the therapeutically effective amount of the compound to be administered ranges from 0.3 to 100 mg (preferably 3 to 50 mg) per kg of body weight per day, such as 3 to 10 mg/kg/day. The intravenous dosage could be in the range, for example, from 0.3 mg/kg to 1.0 mg/kg. Suitable infusion administration should be used, with the infusion rate between 10 ng/kg/min to 100 ng/kg/min. The infusion solution suitable for these purposes could mainly contain, for example, 0.1 ng/ml to 10 mg/ml, preferably 1 ng/ml to 10 mg/ml. The single dosage could contain, for example, 0.1 ng to 10 g active compounds. Therefore, an ampoule for injection administration could contain, for example, 1 mg to 100 mg. The single dose for oral administration, for example, tablet or capsule, could contain 1.0 mg to 1000 mg, usually 10 mg to 600 mg. In the case of the pharmaceutically acceptable salts thereof, therapeutically effective amount is related to the qualities of their corresponding free base. Compounds used for prevention or treatment of diseases mentioned above may be the compounds of Formula (I) itself; however, they preferably combine with acceptable carriers to present in the form of pharmaceutical compositions. Carriers must be compatible, in other words, they should be compatible with other components of the pharmaceutical compositions and be unharmful to the patients. The carriers may be solid, liquid or both, and preferably combine with compound to give single dose, such as tablet, containing 0.05-95 wt % of active compound. Other pharmaceutically active compounds may also exist, including other compounds of formula (I). The pharmaceutical compositions of the present invention can be prepared according to any known pharmaceutical methods, which substantially comprise combining each component with pharmaceutically acceptable carriers and/or adjuvants.

Suitable routes of administration may include, without limitation, oral, rectal, topical, sublingual, and parenteral (e.g. subcutaneous, intramuscular, dermis and intravenous) administration. The preferred routes of administration would be dependent on the subject being treated, the severity of the affliction, and used compound type of Formula (I). Sugar-coated formulations and sugar-coated slow-release formulations are also within the scope of this invention. Preferable formulations are acid-proof and gastric juice-resistant preparations. Suitable gastric juice-resistant coating includes cellulose acetate phthalate, polyvinyl acetate phthalate, hydroxypropyl methylcellulose phthalate and anionic polymer of methyl crotonate.

Pharmaceutical compositions suitable for oral administration are typically independent unit, such as capsule, cachet, troche and tablet, at any circumstances of this unit containing certain amount of compound of Formula (I); powder or granule; solution or suspension in aqueous liquid or non-aqueous liquid; or O/W or W/O emulsion. As mentioned above, the compositions can be prepared according to any known pharmaceutical methods, which comprise a step of contacting the active compound with a carrier (may also comprise one or more other components). Generally, pharmaceutical compositions are prepared as follows: active compounds are mixed uniformly with liquid and/or fine dispersed solid carrier, and then, if necessary, to form the formulations. For example, pellet can be prepared as follows: compressing the powder or granule of compound (appropriately with one or more additional components) to form the formulations. Compressed tablets can be prepared as follows: compressing compounds (appropriately mixed with adhesives, release agents, inert diluent and/or one or more surfactant/dispersant) in free flow form (e.g. powder or granule) in suitable machine. Matrix band can be prepared as follows: powder compound is formulated using inert liquid diluent in suitable machine.

The pharmaceutical composition suitable for oral (sublingual) administration includes troche, which contains compounds of Formula (I) and correctives, such as sucrose/acacia or tragacanth gum; and pastille, which includes compounds of Formula (I) in inert matrix, such as gelatin/glycerol or sucrose/acacia.

The compounds of the present invention (Formula I) may be formulated for parenteral administration. Parenteral formulations are typically sterile aqueous solutions which are isotonic with blood being treated. Suitable means for parenteral administration include intravenous, intramuscular, dermis and subcutaneous. The compounds (Formula I) were mixed with water to give the sterile aqueous solutions isotonic with blood. Injectable aqueous solutions of the present invention generally contain 0.1-5 wt % of active compounds.

The compounds of the present invention (Formula I) may also be formulated preferably as single dose suppository, using one or more conventional suppository bases, e.g. cocoa butter.

The compounds of the invention may be administered topically to the skin. Typical formulations for this purpose include ointments, cream ointments, lotions, pasta, sprays, aerosol and oils. Suitable carrier includes cosmolin, agnolin, polyethylene glycol, spirits and/or combination of two or more carriers above. The concentration of the active compound is generally 0.1-15 wt %, typically 0.5-2 wt %.

The compounds of the invention may also be administered transdermally. Formulations suitable for transdermal administration are typically one-unit patch which can contact tightly with patient's skin. This kind of patch is appropriate to any buffered aqueous solution in which compounds are dissolved in and/or diffused in adhesives or diffused in polymer. Suitable active compounds could be released by electron transport or iontophoresis, as described in, for example, Pharmaceutical Research, 2(6), 318(1986).

Compounds of present invention (Formula I) are significantly effective on lipid metabolism which specially suitable for reducing weight of mammals and keeping weight off after losing weight, as well as using as anorectic. Compounds of present invention (Formula I) are also effective because of their hypotoxicity and low side effect. Compounds of present invention (Formula I) may be administered alone or in combination with one or more other weight-reducing or anorectic active compounds.

Other anorectics active compounds used in the present invention may include compounds as described at chapter 1, weight-loss agent/appetite suppressant, by Roten Liste; or compounds which increase energy transformation of organism, thus resulting in weight loss; or compounds which affect basic metabolism of related organisms, thus increased caloric intake does not lead to the accumulation of fat deposits, and normal caloric intake leads to the decrease of fat deposits. Said compounds are suitable for prevention of overweight or obesity, especially for treatment of overweight or obesity. In addition, said compounds are suitable for prevention of type II diabetes and arteriosclerosis, especially for treatment of type II diabetes and arteriosclerosis; and are suitable for normalization of lipid metabolism and treatment of hypertension. The compounds may serve as MCH antagonists, and are suitable for treatment of sensory disability and other psychiatric symptom, such as depression, aparioneurosis, and schizophrenia, and treatment of circadian rhythm-related disorders and drug abuse.

It is also an aspect of this invention that compounds (Formula I) described herein can be combined with one or more other pharmacological active substances such as antidiabetics, oil/grease repellent, antihypertensive active compounds, antilipemic agents and active compounds used for treatment and/or prevention of complications resulting from diabetes or diabetes related.

Suitable antidiabetics may include, without limitation, insulin, amylin, GLP-1 and/or GLP-2 derivatives, such as antidiabetics published in WO98/08871 by Novo Nordisk A/S, and hypoglycemic active compounds for oral administration.

For oral administration, hypoglycemic active compounds include, in particular, sulfonylurea, biguanide, meglitinide, dioxazolidinedione, thiazolidinedione, glucosidase inhibitors, glucagon receptor antagonist, GLP-1-agonist, potassium channel openers (e.g. patents WO 97/26265 and WO 99/03861 published by Novo Nordisk A/S), insulin sensitizers, insulin receptor kinase activators, inhibitors related to glyconeogenesis and/or liver enzymes stimulated by glycogenolysis (e.g. glycogen phosphorylase inhibitors), modulators related to glucose intake and excretion, compounds related to changing lipid metabolism (e.g. active compounds of anti-hyperlipemia or anti-lipaemia and HMGCoA reductase inhibitors), cholesterol transport/cholesterol intake inhibitors, bile acid reabsorption inhibitors or microsome triglyceride transfer protein (MTP) inhibitors, compounds related to decreasing nutritional agent intake, PPAR/RXR agonist and active compounds targeted on β-cell ATP-dependent potassium channels.

In an embodiment of the present invention, compounds of the invention are administered in combination with insulin.

In another embodiment of the present invention, compounds of the invention are administered in combination with a sulfonylurea, such as tolbutamide, glibenclamide, glimepiride, glipizide, gliquidone, glisoxepide, glibornuride or gliclazide.

In another embodiment of the present invention, compounds of the invention are administered in combination with a biguanide, metforminmetformin for example.

In another embodiment of the present invention, compounds of the invention are administered in combination with a meglitinide, repaglinide for example.

In another embodiment of the present invention, compounds of the invention are administered in combination with a thiazolidinedione, such as troglitazone, ciglitazone, pioglitazone, rosiglitazone or compounds published in WO Pat. No. 97/41097 by Dr. Reddy's Research Foundation, especially the compound 5-[[4-[3,4-2H-3-methyl-4-keto-2-methoxyquizoline)phenyl]methyl]-2,4-thiazolidinedione.

In another embodiment of the present invention, compounds of the invention are administered in combination with an α-sucrosidase inhibitor, such as migltol or acarbose.

In another embodiment of the present invention, compounds of the invention are administered in combination with a drug targeted β-cell ATP-dependent potassium channels, such as tolbutamide, glibenclamide, glimepiride, glipizide, gliclazide or repaglinide.

In another embodiment of the present invention, compounds of the invention are administered in combination with active compounds of anti-hypertension or anti-lipidemia such as colestyramine, colestipol, clofibrate, fenofibrate, gemfibrozil, lovastatin, pravastatin, simvastatin, atorvastatin, cerivastatin, lovastatin, probucol, ezetimibe or cholaxin.

In another embodiment of the present invention, compounds of the invention are administered in combination with one or more drugs described as above, such as sulfonylurea and metformin, sulfonylurea and acarbose, repaglinide and metformin, insulin and sulfonylurea, insulin and metformin, insulin and troglitazone, insulin and lovastatin etc.

Additionally, compounds of this invention may also be administered in combination with one or more oil/grease repellent or appetite control active compounds which include, in particular, CART agonists, NPY antagonists, MC4 agonists, Oxexin antagonists, H3 agonists, TNF agonists, CRF agonists, CRF BP antagonists, urocotin agonists, β3 agonists, MSH agonists, CCK agonists, SSRIs, seronine and NE reuptake inhibitors, 5HT modulators, MAO inhibitors, epibatidine agonists, galanin antagonists, growth hormone, growth hormone releasing compounds, TRH agonists, uncoupling protein 2/3 modulators, leptin agonists, dopamine agonists (e.g. doprexin), esterase/amylase inhibitors, cannagine receptor antagonists, ASP modulators, PPAR modulators, RXR modulators, hCNTF stimulant or TR-β agonists.

In an embodiment of the present invention, an oil/grease repellent is leptin or modified leptin.

In another embodiment of the present invention, an oil/grease repellent is dexamine or phenamine In another embodiment of the present invention, an oil/grease repellent is fenfluramine or isomeride.

In another embodiment of the present invention, an oil/grease repellent is sibutramine or mono-/di-demethylated active metabolite of sibutramine In another embodiment of the present invention, an oil/grease repellent is orlistat In another embodiment of the present invention, an oil/grease repellent is mazindol, amfepramone or phentermine.

Furthermore, compounds of the present invention may be administered in combination with antihypertensive compounds. For instance, anti-hypertension compounds might include β-blockers, such as aiprenolol, atenolol, timolol, pindolol, propranolol and metoprolol; or angiotensin-converting enzyme (ACE) inhibitors such as benazepril, captopril, enalapril, fosinopril, lisinopril and ramipril; or calcium channel blockers such as nifedipine, felodipine, nicardipine, isradipine, nimodipine, diltiazem and verapamil; or α-blockers such as doxazosin, urapidil, prasozin and terazosin. In addition to combination described above, see more reference in The Science and Practice of Pharmacy, 19th edition, Gennaro, editor, Mack Publishing Co., Easton, Pa., 1995 edited by Remington.

Without further elaboration, it should be note that any suitable combination of the stereoisomers of the present invention with one or more above compounds and optionally one or more other pharmacological active substances are within the scope of the present invention.

EXAMPLES

The following detailed examples are given to describe how to prepare the various compounds and/or perform the various processes of the invention and are to be construed as merely illustrative, and not limitations of the preceding disclosure in any way whatever. Those skilled in the art will promptly recognize appropriate variations from the procedures both as to reactants and as to reaction conditions and techniques.

Example 1 synthesis of 1-[1-(4-chlorophenyl)cyclobutyl]-3-methylbutylamine and its optical isomers 1. Synthesis of racemic 1-[1-(4-chlorophenyl)cyclobutyl]-3-methylbutylamine (II)

As described in article (Chinese Journal of Pharmaceuticals, 2001, 32(8): 337-339), p-chlorobenzyl cyanide was condensed with 1,3-dibromopropane, cycled to give cyclobutyl inter mediate, and then through Grignard reaction and reduction reaction to give title compound (56.2% yield).

2. Resolution Example 20.3 g of racemic 1-[1-(4-chlorophenyl)cyclobutyl]-3-methylbutylamine obtained in step 1 was dissolved in 300 mL mixture solvent of acetone/water/methanol (1:0.13:0.7,V/V). L(+)-tartaric acid (12.1 g) was added to the mixture and refluxed for 0.5 hours. The mixture was cooled to room temperature, and kept at room temperature for 2-4 days to crystallization. The crystals were filtered off, washed with cold acetone/water (100 mL/13 mL), and dried to give solid (10.3 g, 33% yield). Acetonitrile 25 g crystals above and acetonitrile/water/ethanol (300 mL/65 mL/30 mL) were refluxed for 1 hour, and then cooled to room temperature to give white solid (18 g, 72% yield). The solid were treated with alkaline to give free base (S)-1-[1-(4-chlorophenyl)cyclobutyl]-3-methylbutylamine (II-S) (optical purity 99.7%).

As described above, D-(−)-tartaric acid was used to resolute racemic compound II to give another optical isomer (75.2% yield). This optical isomer were treated with alkaline to give free base (R)-1-[1-(4-chlorophenyl)cyclobutyl]-3-methylbutylamine (II-R) (optical purity 99.4%).

In examples 1, 3-6, and 8-11, chiral column was used to determine the optical purity of optical isomers, and it was shown that the optical purity of all compounds were above 99.0%. The chiral column was ULTRON ES—OVM (150 mm×4.6 mm), mobile phase 0.01M $KH_2PO_4/CH_3OH$ (70:30), and UV absorbance at 200 nm.

Example 2

Synthesis of 2-(Boc-amino)-N-{1-[1-(4-chlorophenyl)cyclobutyl]-3-methylbutyl}-3-methylvaleramide

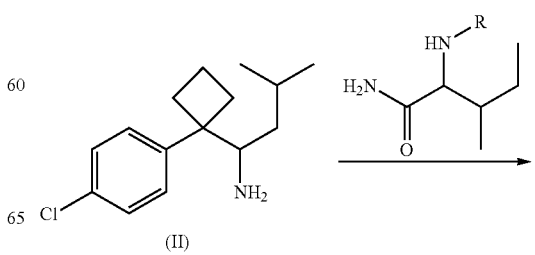

-continued

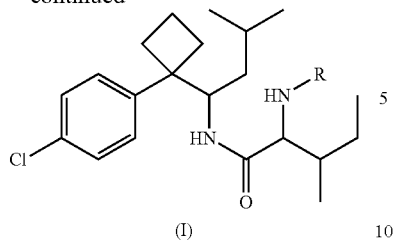

(I)

250 mg of 1-[1-(4-chlorophenyl)cyclobutyl]-3-methylbutylamine (II) and 210 mg of Boc-isoleucine (R in Formula is Boc) was dissolved in anhydrous THF (5 mL). 220 mg DCC was dissolved in 25 mL anhydrous THF. The solution of DCC in THF was added dropwisely into the reaction solution, and then stirred overnight at room temperature to give white precipitate. The solid was filtered off and washed for at least three times with anhydrous ethyl ether. The filtrate and washed ethyl ether were collected, evaporated and purified by column chromatography to give title compound 2-(Boc-amino)-N-{1-[1-(4-chlorophenyl)cyclobutyl]-3-methylbutyl}-3-methylvaleramide (Formula I, wherein R is Boc).

Molecular weight: 465.07 ($C_{26}H_{41}ClN_2O_3$).

MS (ESI) 465 ($M^+$).

Elemental analysis

Theoretical values: C (%) 67.15; H (%) 8.88; N (%) 6.02; Cl (%) 7.62

Measured values: C (%) 67.05; H (%) 8.76; N (%) 6.01; Cl (%) 7.55.

Example 3

Synthesis of (2S,3S)-2-(Boc-amino)-N-{(S)-1-[1-(4-chlorophenyl)cyclobutyl]-3-methylbutyl}-3-methylvaleramide By similar method as example 2, resolved (S)-1-[1-(4-chlorophenyl)cyclobutyl]-3-methylbutylamine (II-S) (250 mg) was condensed with Boc-L-isoleucine (210 mg) to give the title compound (2S,3S)-2-(Boc-amino)-N-{(S)-1-[1-(4-chlorophenyl)cyclobutyl]-3-methylbutyl}-3-methylvaleramide.

Molecular weight: 465.07 ($C_{26}H_{41}ClN_2O_3$).

MS (ESI) 465 ($M^+$).

Formula as follows:

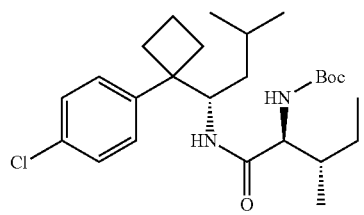 [SMILES: CC[C@H](C)[C@H](NC(=O)OC(C)(C)C)C(=O)N[C@@H](CC(C)C)C1(c2ccc(Cl)cc2)CCC1]

Elemental analysis

Theoretical values: C (%) 67.15; H (%) 8.88; N (%) 6.02; Cl (%) 7.62

Measured values: C (%) 66.98; H (%) 8.92; N (%) 6.15; Cl (%) 7.48.

Example 4

Synthesis of (2S,3S)-2-(Boc-amino)-N-{(R)-1-[1-(4-chlorophenyl)cyclobutyl]-3-methylbutyl}-3-methylvaleramide By similar method as example 2, resolved (R)-1-[1-(4-chlorophenyl)cyclobutyl]-3-methylbutyl was condensed with Boc-L-isoleucine, and purified to give title compound (2S,3S)-2-(Boc-amino)-N-{(R)-1-[1-(4-chlorophenyl)cyclobutyl]-3-methylbutyl}-3-methylvaleramide.

Molecular weight: 465.07 ($C_{26}H_{41}ClN_2O_3$).

MS (ESI) 465 ($M^+$).

Formula as follows:

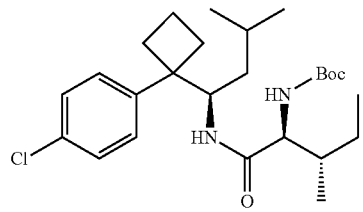 [SMILES: CC[C@H](C)[C@H](NC(=O)OC(C)(C)C)C(=O)N[C@H](CC(C)C)C1(c2ccc(Cl)cc2)CCC1]

Elemental analysis

Theoretical values: C (%) 67.15; H (%) 8.88; N (%) 6.02; Cl (%) 7.62

Measured values: C (%) 67.30; H (%) 9.07; N (%) 5.99; Cl (%) 7.88.

Example 5

Synthesis of (2R,3R)-2-(Boc-amino)-N-{(S)-1-[1-(4-chlorophenyl)cyclobutyl]-3-methylbutyl}-3-methylvaleramide By similar method as example 2, resolved (S)-1-[1-(4-chlorophenyl)cyclobutyl]-3-methylbutyl was condensed with Boc-D-isoleucine, and purified to give title compound (2R,3R)-2-(Boc-amino)-N-{(S)-1-[1-(4-chlorophenyl)cyclobutyl]-3-methylbutyl}-3-methylvaleramide.

Molecular weight: 465.07 (C26H41ClN2O3).

MS (ESI) 465 ($M^+$).

Formula as follows:

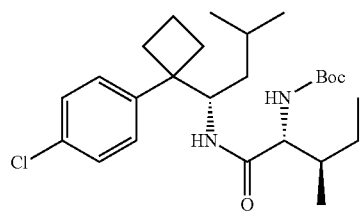 [SMILES: CC[C@@H](C)[C@@H](NC(=O)OC(C)(C)C)C(=O)N[C@@H](CC(C)C)C1(c2ccc(Cl)cc2)CCC1]

Elemental analysis

Theoretical values: C (%) 67.15; H (%) 8.88; N (%) 6.02; Cl (%) 7.62

Measured values: C (%) 67.05; H (%) 8.76; N (%) 6.01; Cl (%) 7.55.

Example 6

Synthesis of (2R,3R)-2-(Boc-amino)-N-{(R)-1-[1-(4-chlorophenyl)cyclobutyl]-3-methylbutyl}-3-methylvaleramide By similar method as example 2, resolved (R)-1-[1-(4-chlorophenyl)cyclobutyl]-3-methylbutyl was condensed with Boc-D-isoleucine, and purified to give title compound (2R,3R)-2-(Boc-amino)-N-{(R)-1-[1-(4-chlorophenyl)cyclobutyl]-3-methylbutyl}-3-methylvaleramide.

Molecular weight: 465.07 ($C_{26}H_{41}ClN_2O_3$).

MS (ESI) 465 ($M^+$).

Formula as follows:

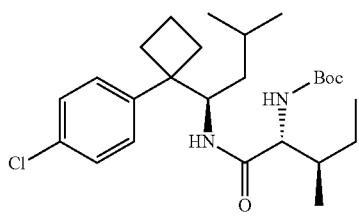 [SMILES: CC[C@@H](C)[C@@H](NC(=O)OC(C)(C)C)C(=O)N[C@H](CC(C)C)C1(c2ccc(Cl)cc2)CCC1]

Elemental analysis

Theoretical values: C (%) 67.15; H (%) 8.88; N (%) 6.02; Cl (%) 7.62

Measured values: C (%) 67.10; H (%) 8.82; N (%) 6.10; Cl (%) 7.60.

Example 7

Synthesis of 2-amino-N-{1-[1-(4-chlorophenyl)cyclobutyl]-3-methylbutyl}-3-methylvaleramide hydrochloride 2-(Boc-amino)-N-{1-[1-(4-chlorophenyl)cyclobutyl]-3-methylbutyl}-3-methylvaleramide (Example 2) was dissolved in $CF_3COOH$. This solution was stirred at room temperature for 3 hours, and then evaporated under vacuum to remove $CF_3COOH$. The produced white solid was collected, dissolved in anhydrous ethyl ether, and washed repeatedly with saturated sodium bicarbonate until pH of the eluate was neutral. This solution of ethyl ether was then washed with saturated sodium chloride for 2-3 times, dried over anhydrous sodium sulfate, and concentrated. The crude product was purified by column chromatography to give 2-amino-N-{1-[1-(4-chlorophenyl)cyclobutyl]-3-methylbutyl}-3-methylvaleramide.

2-amino-N-{1-[1-(4-chlorophenyl)cyclobutyl]-3-methylbutyl}-3-methylvaleramide obtained was dissolved in small amount of anhydrous ethyl ether. Ethyl ether hydrochloride was then added to the solution and large amount of white precipitate was formed. The precipitate was washed with anhydrous ethyl ether, and then recrystallized in anhydrous ethanol and anhydrous ethyl ether to give the title compound 2-amino-N-{1-[1-(4-chlorophenyl)cyclobutyl]-3-methylbutyl}-3-methylvaleramide hydrochloride.

Molecular weight: 401.5 ($C_{21}H_{33}ClN_2O \cdot HCl$).

Free base MS (ESI) 365 ($M^+$).

Formula as follows:

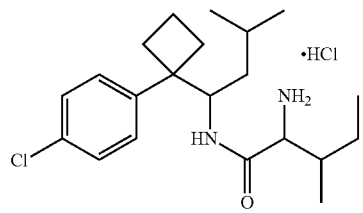 [SMILES: CCC(C)C(N)C(=O)NC(CC(C)C)C1(c2ccc(Cl)cc2)CCC1 ; Cl]

$^1$H NMR ($CDCl_3$) δ 8.50 (S, 2H, signal disappeared after $D_2O$ exchange), 7.15 (d, 2H), 7.05 (d, 2H), 4.53 (d, 1H), 3.97 (S, 1H, signal disappeared after $D_2O$ exchange), 2.06-2.30 (m, 6H), 1.57-1.61 (m, 4H), 0.81-1.19 (m, 15H).

Elemental analysis

Theoretical values: C (%) 62.82; H (%) 8.54; N (%) 6.98; Cl (%) 17.66

Measured values: C (%) 62.75; H (%) 8.46; N (%) 6.89; Cl (%) 17.63

Example 8

Synthesis of (2S,3S)-2-amino-N-{(S)-1-[1-(4-chlorophenyl)cyclobutyl]-3-methylbutyl}-3-methylvaleramide hydrochloride Boc group in (2S,3S)-2-(Boc-amino)-N-{(S)-1-[1-(4-chlorophenyl)cyclobutyl]-3-methylbutyl}-3-methylvaleramide (example 3) was removed in $CF_3COOH$ by similar method of example 7 to give (2S,3S)-2-amino-N-{(S)-1-[1-(4-chlorophenyl)cyclobutyl]-3-methylbutyl}-3-methylvaleramide.

(2S,3S)-2-amino-N-{(S)-1-[1-(4-chlorophenyl)cyclobutyl]-3-methylbutyl}-3-methylvaleramide obtained was dissolved in small amount of anhydrous ethyl ether. Ethyl ether hydrochloride was then added to the solution and large amount of white precipitate was formed. The precipitate was washed with anhydrous ethyl ether, and then recrystallized in anhydrous ethanol and anhydrous ethyl ether to give the title compound (2S,3S)-2-amino-N-{(S)-1-[1-(4-chlorophenyl)cyclobutyl]-3-methylbutyl}-3-methylvaleramide hydrochloride.

Molecular weight: 401.5 ($C_{21}H_{33}ClN_2O \cdot HCl$).

Free base MS (ESI) 365 ($M^+$).

Formula as follows:

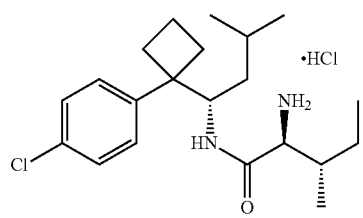 [SMILES: CC[C@H](C)[C@H](N)C(=O)N[C@@H](CC(C)C)C1(c2ccc(Cl)cc2)CCC1 ; Cl]

$^1$H NMR ($CDCl_3$) δ 8.52 (S, 2H, signal disappeared after $D_2O$ exchange), 7.21 (d, 2H); 7.03 (d, 2H), 4.61 (d, 1H), 3.94 (S, 1H, signal disappeared after $D_2O$ exchange), 2.04-2.27 (m, 6H), 1.51-1.63 (m, 4H), 0.90-1.21 (m, 15H).

Elemental analysis

Theoretical values: C (%) 62.82; H (%) 8.54; N (%) 6.98; Cl (%) 17.66

Measured values: C (%) 62.80; H (%) 8.62; N (%) 7.03; Cl (%) 17.57

Example 9

Synthesis of (2S,3S)-2-amino-N-{(R)-1-[1-(4-chlorophenyl)cyclobutyl]-3-methylbutyl}-3-methylvaleramide hydrochloride Boc group in (2S,3S)-2-(Boc-amino)-N-{(R)-1-[1-(4-chlorophenyl)cyclobutyl]-3-methylbutyl}-3-methylvaleramide (example 4) was removed in CF3COOH by similar method of example 7 to give (2S,3S)-2-amino-N-{(R)-1-[1-(4-chlorophenyl)cyclobutyl]-3-methylbutyl}-3-methylvaleramide.

(2S,3S)-2-amino-N-{(R)-1-[1-(4-chlorophenyl)cyclobutyl]-3-methylbutyl}-3-methylvaleramide obtained was dissolved in small amount of anhydrous ethyl ether. Ethyl ether hydrochloride was then added to the solution and large amount of white precipitate was formed. The precipitate was washed with anhydrous ethyl ether, and recrystallized in anhydrous ethanol and anhydrous ethyl ether to give the title compound (2S,3S)-2-amino-N-{(R)-1-[1-(4-chlorophenyl)cyclobutyl]-3-methylbutyl}-3-methylvaleramide hydrochloride.

Molecular weight: 401.5 ($C_{21}H_{33}ClN_2O \cdot HCl$).

Free base MS (ESI) 365 (M$^+$).

Formula as follows:

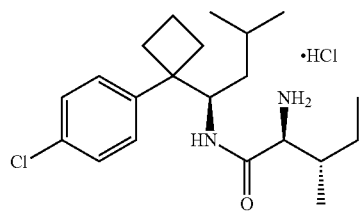 [SMILES: CC[C@H](C)[C@H](N)C(=O)N[C@H](CC(C)C)C1(c2ccc(Cl)cc2)CCC1 ; Cl]

$^1$H NMR (CDCl$_3$) δ 8.47 (S, 2H, signal disappeared after D$_2$O exchange), 7.21 (d, 2H), 7.04 (d, 2H), 4.49 (d, 1H), 4.01 (S, 1H, signal disappeared after D$_2$O exchange), 2.05-2.32 (m, 6H), 1.56-1.63 (m, 4H), 0.86-1.13 (m, 15H).

Elemental analysis

Theoretical values: C (%) 62.82; H (%) 8.54; N (%) 6.98; Cl (%) 17.66

Measured values: C (%) 62.91; H (%) 8.59; N (%) 6.93; Cl (%) 17.53

Example 10

Synthesis of (2R,3R)-2-amino-N-{(S)-1-[1-(4-chlorophenyl)cyclobutyl]-3-methylbutyl}-3-methylvaleramide hydrochloride Boc group in (2R,3R)-2-(Boc-amino)-N-{(S)-1-[1-(4-chlorophenyl)cyclobutyl]-3-methylbutyl}-3-methylvaleramide (example 5) was removed in CF3COOH by similar method of example 7 to give (2R,3R)-2-amino-N-{(S)-1-[1-(4-chlorophenyl)cyclobutyl]-3-methylbutyl}-3-methylvaleramide.

(2R,3R)-2-amino-N-{(S)-1-[1-(4-chlorophenyl)cyclobutyl]-3-methylbutyl}-3-methylvaleramide obtained was dissolved in small amount of anhydrous ethyl ether. Ethyl ether hydrochloride was then added to the solution and large amount of white precipitate was formed. The precipitate was washed with anhydrous ethyl ether, and recrystallized in anhydrous ethanol and anhydrous ethyl ether to give the title compound (2R,3R)-2-amino-N-{(S)-1-[1-(4-chlorophenyl)cyclobutyl]-3-methylbutyl}-3-methylvaleramide hydrochloride.

Molecular weight: 401.5 ($C_{21}H_{33}ClN_2O \cdot HCl$).

Free base MS (ESI) 365 (M$^+$).

Formula as follows:

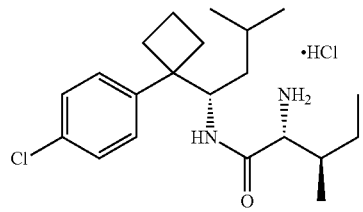 [SMILES: CC[C@@H](C)[C@@H](N)C(=O)N[C@@H](CC(C)C)C1(c2ccc(Cl)cc2)CCC1 ; Cl]

$^1$H NMR (CDCl$_3$) δ 8.51 (S, 2H, signal disappeared after D$_2$O exchange), 7.14 (d, 2H), 7.05 (d, 2H), 4.55 (d, 1H), 3.99 (S, 1H, signal disappeared after D$_2$O exchange), 2.05-2.15 (m, 6H), 1.51-1.60 (m, 4H), 0.95-1.05 (m, 15H).

Elemental analysis

Theoretical values: C (%) 62.82; H (%) 8.54; N (%) 6.98; Cl (%) 17.66

Measured values: C (%) 62.78; H (%) 8.60; N (%) 7.12; Cl (%) 17.53

Example 11

Synthesis of (2R,3R)-2-amino-N-{(R)-1-[1-(4-chlorophenyl)cyclobutyl]-3-methylbutyl}-3-methylvaleramide hydrochloride Boc group in (2R,3R)-2-(Boc-amino)-N-{(R)-1-[1-(4-chlorophenyl)cyclobutyl]-3-methylbutyl}-3-methylvaleramide (example 6) was removed in CF3COOH by similar method of example 7 to give (2R,3R)-2-amino-N-{(R)-1-[1-(4-chlorophenyl)cyclobutyl]-3-methylbutyl}-3-methylvaleramide.

(2R,3R)-2-amino-N-{(R)-1-[1-(4-chlorophenyl)cyclobutyl]-3-methylbutyl}-3-methylvaleramide obtained was dissolved in small amount of anhydrous ethyl ether. Ethyl ether hydrochloride was then added to the solution and large amount of white precipitate was formed. The precipitate was washed with anhydrous ethyl ether, and recrystallized in anhydrous ethanol and anhydrous ethyl ether to give the title compound (2R,3R)-2-amino-N-{(R)-1-[1-(4-chlorophenyl)cyclobutyl]-3-methylbutyl}-3-methylvaleramide hydrochloride.

Molecular weight: 401.5 ($C_{21}H_{33}ClN_2O \cdot HCl$).

Free base MS (ESI) 365 (M$^+$).

Formula as follows:

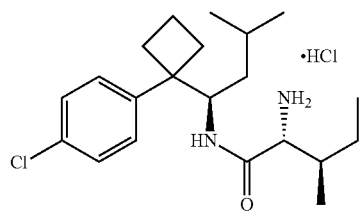 [SMILES: CC[C@@H](C)[C@@H](N)C(=O)N[C@H](CC(C)C)C1(c2ccc(Cl)cc2)CCC1 ; Cl]

¹H NMR (CDCl₃) δ 8.48 (S, 2H, signal disappeared after D₂O exchange), 7.17 (d, 2H), 7.05 (d, 2H), 4.51 (d, 1H), 3.91 (S, 1H, signal disappeared after D₂O exchange), 2.01-2.28 (m, 6H), 1.54-1.67 (m, 4H), 0.93-1.22 (m, 15H).

Elemental analysis

Theoretical values: C (%) 62.82; H (%) 8.54; N (%) 6.98; Cl (%) 17.66

Measured values: C (%) 62.97; H (%) 8.59; N (%) 6.83; Cl (%) 17.54

Example 12

Synthesis of 2-(R-amino)-N-{1-[1-(4-chlorophenyl) cyclobutyl]-3-methylbutyl}-3-methylvaleramide hydrochloride and its optical isomers By similar method as example 2, Boc-isoleucine was replaced with Fmoc-isoleucine, formyl-isoleucine, acetyl-isoleucine, chloroacetyl-isoleucine, benzoyl-isoleucine, Cbz-isoleucine, respectively, to give 2-(R-amino)-N-{1-[1-(4-chlorophenyl)cyclobutyl]-3-methylbutyl}-3-methylvaleramide. Herein R represents Fmoc-, formyl-, acetyl-, chloroacetyl-, benzoyl-, and Cbz-, respectively.

When R is Fmoc, Molecular weight 587.2 ($C_{36}H_{43}ClN_2O_3$), MS (ESI) 588 ($M^+$);

When R is formyl-, molecular weight 392.97 ($C_{22}H_{33}ClN_2O_2$), MS (ESI) 394 ($M^+$);

When R is acetyl-, molecular weight 406.99 ($C_{23}H_{35}ClN_2O_2$), MS (ESI) 407 ($M^+$);

When R is chloroacetyl-, molecular weight 441.43 ($C_{23}H_{34}Cl_2N_2O_2$), MS (ESI) 442 ($M^+$);

When R is benzoyl-, molecular weight 469.07 ($C_{28}H_{37}ClN_2O_2$), MS (ESI) 470 ($M^+$);

When R is Cbz, molecular weight 499.09 ($C_{29}H_{39}ClN_2O_3$), MS (ESI) 501 ($M^+$).

Similarly, using methods of example 3-6, 4 optical isomers of each of the title compound of example 12 were prepared.

Compounds with R being H were obtained according to the methods of example 7-11 using 4 optical isomers of each title compound of example 12 as raw material.

Above specific examples describe the preparation of compounds of Formula (I) and optical isomers thereof. It should be understood that above examples should not be considered as the limitation of the present invention. The reaction conditions and the parameters may be modified by a skilled person in the field of organic synthesis.

With respect to the applications, compounds of present invention can be used as active ingredients in the preparation of weight-reducing drugs. Efficacy of the compounds of present invention is shown as follows.

The experimental Study of Weight-Reducing on Pharmacodynamics

1. Materials
1.1 Animals:

Same numbers of male and female weanling Sprague Dawley rats (clean grade, 43.3±8.5 g) were obtained from Laboratory Animal Center (Chongqing medical university, China) (Certificate of Approval for Environmental Facilities: SYXK (Yu) 20020007; Certificate of Approval for animal: SCXK (Yu) 20020001).

1.2 Medicine and Preparation:

racemic compound hydrochloride of example 7, optical isomers of examples 8, 9, 10 and 11, and positive control Sibutramine Hydrochloride were dissolved in 1% CMC-Na.

1.3 Test Instrument:

TGL-16 table model high speed centrifuge (Shanghai Medical Instruments Factory NO. 6); KDC centrifuge (Huicheng Radio Factory, Guangzhou); Sartorius electronic balance (GERMANY); Medical refrigerator temperature (SANYO, JAPAN); thermostat water bath tank (Beijing Xicheng district medical apparatus factory); VXH-3 Mini Vortex Mixer (Shanghai Yuejin Medical Apparatus Facotry).

1.4 Nutrition Feed:

the recipe of nutrition feed and basal feed are as follows:
Basal Feed:
Barley flour 20%, dehydrated vegetable 10%, bean flour 20%, corn flour 16%, yeast 1%, wheat bran 16%, fish meal 10%, bone meal 5%, salt 2%.

Milk Powder:
Oleum jecoris piscis concentratum, lard, fresh bean sprouts and eggs were all purchased from market.

Nutrient Feed:
In the 100 g basal feed, milk powder 10 g, lard 10 g, egg 1 piece, fresh bean sprouts 250 g, oleum jecoris piscis concentratum 10 drops (including VA 1700 u, VD1700 u) were added.

2. Method
2.1 Establishment and Grouping of Obese Animal Model

Weanling SD rats were randomly allocated to compound groups with large, middle, small dosages; positive control Sibutramine Hydrochloride groups with large, middle, small dosages; and obese animal model group and blank control group (n=5/group for male; n=5/group for female).

The experimental animals in blank control group were feed with normal feed, and animals in other groups were feed with nutrient feed. All animals have abundant feed for 24 h and can eat casually.

2.2 Dosage for Drug

Experimental animals in each group were administrated with corresponding drugs once a day at 9 am for 30 days, with a dosage of 1 ml/100 g body weight. The dosage corresponds to clinical dosage of 10 mg/person/day for Sibutramine, which is transformed according to the equivalent dosage between human and rat. Large dosage group adopts 1.2 mg/kg; middle dosage group adopts 0.6 mg/kg, and small dosage group adopts 0.3 mg/kg. Obese animal model group: 10 mg/kg of 1% CMC-Na solution; blank control group: 10 mg/kg of 1% CMC-Na solution.

3. Measurement
3.1 Body Weight:
Measurements were taken of daily body weight; general status; hair; eye, mouth and nose secretions; feces, urinate and activities.
3.2 Fat Weight:
Intraperitoneal and perirenal fat were weighted, and the fat weight coefficient was calculated by body weight.
4. Result
4.1 Observations on Animal Behaviour and Organs
On trial, the animal behaviour; general status; hair; mouth and nose secretions feces; urinate; activities and diet of the rats did not change. After 30 days, rat size of model group is fat, while they are thin in the blank control and experimental groups. At the end of the experiment, rats were killed, and anatomical observations of liver, heart, kidney and reproductive system are normal.

4.2 Effects of Test Drugs on the Body Weight in Rats

As shown in table 1, the body weight and fat weight observed before the experiment were significantly different from those observed after the experiment. We found that the body weight and fat weight of experimental groups were significantly different from those of model group.

TABLE 1

Effects of test drugs on the body weight of rats

| group | Initial average body weight (g) | Final average body weight (g) | Average added multiplier of body weight[#] | Average fat weight (g) | Average fat weight coefficient[##] |
|---|---|---|---|---|---|
| Blank control | 41.7 | 154.4 | 2.7 | 1.0 | 0.7 |
| Model | 42.1 | 217.0 | 4.2 | 3.2 | 1.5 |
| Sibutramine, large dosage | 42.3 | 165.7 | 2.9 | 1.9 | 1.1 |
| Sibutramine, middle dosage | 43.3 | 183.2 | 3.2 | 1.8 | 1.0 |
| Sibutramine, small dosage | 42.5 | 185.7 | 3.4 | 1.9 | 1.0 |
| Example 7 large dosage | 42.2 | 176.2 | 3.2 | 2.0 | 1.1 |
| Example 7 middle dosage | 42.4 | 180.5 | 3.3 | 2.1 | 1.2 |
| Example 7 small dosage | 43.1 | 186.9 | 3.3 | 2.2 | 1.2 |
| Example 8 large dosage | 43.8 | 175.2 | 3.0 | 1.7 | 1.0 |
| Example 8 middle dosage | 44.2 | 185.6 | 3.2 | 1.9 | 1.0 |
| Example 8 small dosage | 42.9 | 188.9 | 3.4 | 2.0 | 1.1 |
| Example 9 large dosage | 43.3 | 156.1 | 2.6 | 1.4 | 0.9 |
| Example 9 middle dosage | 45.4 | 167.9 | 2.7 | 1.5 | 0.9 |
| Example 9 small dosage | 44.3 | 168.1 | 2.8 | 1.5 | 0.9 |
| Example 10 large dosage | 43.4 | 173.9 | 3.0 | 1.9 | 1.1 |
| Example 10 middle dosage | 42.5 | 180.4 | 3.2 | 2.0 | 1.2 |
| Example 10 small dosage | 43.6 | 185.0 | 3.2 | 2.1 | 1.2 |
| Example 11 large dosage | 42.8 | 162.4 | 2.8 | 1.8 | 1.1 |
| Example 11 middle dosage | 43.3 | 173.2 | 3.0 | 1.9 | 1.1 |
| Example 11 small dosage | 43.1 | 181.0 | 3.2 | 2.1 | 1.2 |

All the compounds in the table were hydrochloride.
[#]Average added multiplier of body weight = (final average body weight-initial average body weight)/initial average body weight.
[##]Average fat weight coefficient = average fat weight/final average body weight.

The results of the present study suggest that the body weight, fat weight and fat weight coefficient of the rats from all the experimental groups decreased respectively, which were significantly different from those observed in the model group. When compared with Sibutramine, the compound of example 9 can decreased the body weight evidently. It can be seen that the effects of decreasing fat weight were better in treatment group than in model group, among which the compound of example 9 is the best. On the other hand, it has significantly better effect than Sibutramine.

On trial, we observed the effect of compounds on the animal physical sign. The results of the present study suggest that anatomical observations of liver, heart, kidney and reproductive system were normal.

We tested the effects of the final compounds of examples 2-6 and 12 on anti-obesity. It was demonstrated that they were able to reduce the body weight and fat weight in rats, and had effects on weight-reducing and reducing lipid.

Toxicity Test in Mice

Toxicity testing was carried out by skilled persons in the art through common test method for toxicity.

Healthy mice (18-22 g) were randomly divided into blank group, positive control group (Sibutramine HCl group) and compound groups, with 10 mice per group. The compounds were dissolved in physiological saline at certain concentration and were orally administered daily for 7 consecutive days. Neither deaths nor behavioral abnormalities were observed during the observation, which showed that the toxicity of compounds had no significantly difference in toxicity with positive control group.

INDUSTRIAL APPLICATION

The compounds and their compositions provided in the present invention can be prepared as medicine for treating obesity, and thus are industrially applicable.

5. The method of claim 4, wherein the pharmaceutically acceptable salts are hydrochloride salts.
6. The method of claim 1, wherein the compounds comprises at least one of the following structure:
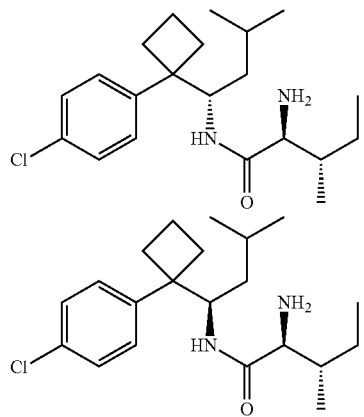
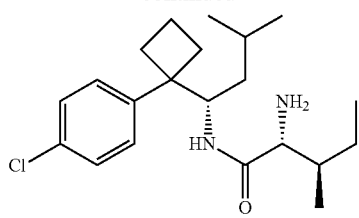
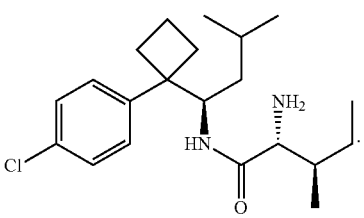

What is claimed is:

1. A method for treating obesity or reducing weight in a subject in need thereof, comprising administering to the subject a phenylcyclobutylamide derivative comprising a compound of formula (I), a stereoisomer thereof, or a pharmaceutically acceptable salt thereof:

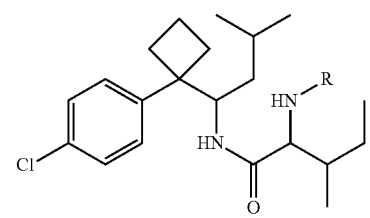

(I)

wherein, R is H or acyl group containing 1 to 16 carbon atoms.

2. The method of claim 1, wherein the acyl group containing 1 to 16 carbon atoms is formacyl, acetyl, haloacetyl, benzoyl, benzyloxycarbonyl (Cbz), t-butyloxycarbonyl (Boc), or 9-fluorenylmethoxylcarbonyl (Fmoc).

3. The method of claim 1, wherein R is H.

4. The method of claim 1, wherein the compounds are at least one selected from the group consisting of 2-amino-N-{1-[1-(4-chlorophenyl)cyclobutyl]-3-methylbutyl}-3-methylpentanamide and the optical isomers thereof: (2S,3S)-2-amino-N-{(S)-1-[1-(4-chlorophenyl)cyclobutyl]-3-methylbutyl}-3-methyl pentanamide; (2S,3S)-2-amino-N-{(R)-1-[1-(4-chlorophenyl)cyclobutyl]-3-methylbutyl}-3-methylpentanamide; (2R,3R)-2-amino-N-{(S)-1-[1-(4-chlorophenyl)cyclobutyl]-3-methylbutyl}-3-methylpentanamide; (2R,3R)-2-amino-N-{(R)-1-[1-(4-chlorophenyl)cyclobutyl]-3-methylbutyl}-3-methyl pentanamide; and the pharmaceutically acceptable salts of these compounds.